United States Patent
Osone et al.

(10) Patent No.: US 8,648,723 B2
(45) Date of Patent: Feb. 11, 2014

(54) BIOLOGICAL INFORMATION MONITORING SYSTEM

(75) Inventors: Kazuo Osone, Tokyo (JP); Masato Semba, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 277 days.

(21) Appl. No.: 12/861,278

(22) Filed: Aug. 23, 2010

(65) Prior Publication Data
US 2011/0043366 A1 Feb. 24, 2011

(30) Foreign Application Priority Data
Aug. 24, 2009 (JP) .................................. 2009-193696

(51) Int. Cl.
G08B 23/00 (2006.01)
(52) U.S. Cl.
USPC ........ 340/573.1; 340/292; 340/515; 600/300; 600/310
(58) Field of Classification Search
USPC ................ 340/573.1, 292, 515; 600/300, 310
See application file for complete search history.

(56) References Cited

U.S. PATENT DOCUMENTS

| | | | |
|---|---|---|---|
| 5,103,214 A * | 4/1992 | Curran et al. | 340/691.1 |
| 7,962,188 B2 * | 6/2011 | Kiani et al. | 600/310 |
| 2003/0128126 A1 | 7/2003 | Burbank et al. | |
| 2004/0172222 A1 | 9/2004 | Simpson et al. | |
| 2007/0000824 A1 | 1/2007 | Bock et al. | |
| 2008/0319544 A1 | 12/2008 | Yaegashi | |

FOREIGN PATENT DOCUMENTS

| | | |
|---|---|---|
| JP | 2585040 Y2 | 11/1998 |
| JP | 2009-223 A | 1/2009 |
| JP | 2009-510631 A | 3/2009 |
| WO | 2007/041329 A1 | 4/2007 |

OTHER PUBLICATIONS

Extended European Search Report issued on Jan. 11, 2011 in the corresponding European Patent Application No. 10173835.9.
Communication dated Feb. 19, 2013, from the Japanese Patent Office in counterpart Japanese application No. 2009-193696.
Office Action, dated Oct. 30, 2013, issued by the Japanese Patent Office, in counterpart Application No. 2009-193696.

* cited by examiner

*Primary Examiner* — Brian Zimmerman
*Assistant Examiner* — Bhavin M Patel
(74) *Attorney, Agent, or Firm* — Sughrue Mion, PLLC

(57) ABSTRACT

A biological information monitoring system includes: an alarm generator which generates an alarm signal indicative of an abnormality of biological information of a patient, or an abnormality of a unit related to monitoring of biological information of a patient, or an abnormality due to an operation of a unit related to monitoring of biological information of a patient; a first output generator which performs a first output based on the alarm signal; a detector which detects information related to the first output; a second output generator which performs a second output being independent from the first output; and a warning controller which controls the second output generator to perform the second output based on the detected information related to the first output.

11 Claims, 10 Drawing Sheets

BIOLOGICAL INFORMATION MONITORING SYSTEM

BACKGROUND OF THE INVENTION

The present invention relates to a biological information monitoring system which performs a warning output based on an alarm signal indicative of an abnormality of biological information (vital alarm), that indicative of an abnormality of an apparatus or a sensor (technical alarm), or that indicative of an abnormality which is noticed by the patient and is informed by operating an apparatus such as a nurse call apparatus, and more particularly to a biological information monitoring system in which a notification is issued in the case where a warning output due to an alarm signal is not adequately performed, thereby preventing an unexpected situation from occurring.

As a system of this kind, JP-A-2009-510631 discloses the following related-art system. In the related-art system, in the case where a caregiver, nurse, or the like who is the observer of the patient does not perform, for example, an operation of pressing an acknowledge button in response to occurrence to a warning state, a reminder tone of large volume is output from a speaker for performing the warning, or another speaker different therefrom.

In the related-art system, however, there is a problem in that the function can be stopped by, for example, an operation of reducing the sound volume. Recently, particularly, the sound volume of a warning system used in a medical site is reduced, and hence there arises a case where the observer fails to notice a warning.

The above-described related-art system cannot cope with a problem in that, when there is a failure in a transmission path of an alarm signal for outputting a warning output, the warning output is not performed.

In the case where the observer is in a noisy environment, moreover, it may be supposed that, even when a warning output is performed at an adequate sound volume, the alarm sound cannot be heard.

SUMMARY

It is therefore an object of the invention to provide a biological information monitoring system which, in accordance with a state of an alarm output, can perform a warning output that is independent from the alarm output. Specifically, it is an object of the invention to provide a biological information monitoring system in which, in the case where a warning output is not performed although an alarm signal is produced, the warning output is performed, and in which, even when an operation of reducing the volume or turning off the warning output is performed, a signal indicative of a warning state can be surely output.

In order to achieve the object, according to the invention, there is provided a biological information monitoring system comprising: an alarm generator which generates an alarm signal indicative of an abnormality of biological information of a patient, or an abnormality of a unit related to monitoring of biological information of a patient, or an abnormality due to an operation of a unit related to monitoring of biological information of a patient; a first output generator which performs a first output based on the alarm signal; a detector which detects information related to the first output; a second output generator which performs a second output being independent from the first output; and a warning controller which controls the second output generator to perform the second output based on the detected information related to the first output.

The warning controller may control the second output generator to perform the second output based on at least one of the alarm signal and a notification signal which is based on the alarm signal and indicative of presence/absence of the alarm signal.

The information related to the first output which is detected by the detector may include presence/absence of the alarm signal in a path from the alarm generator to the first output generator.

The alarm generator may be disposed in one of a remote device which is remotely connected to a monitor device which monitors the biological information of the patient and the monitor, and the first output generator and the detector may be disposed in the remote device.

The alarm generator, the first output generator, the detector, the second output generator, and the warning controller may be disposed in a monitor device which monitors the biological information of the patient.

The biological information monitoring system may further include: a display unit; and a body unit which sends display information to the display unit. The first output generator and the detector may be disposed in the display unit, and the second output generator and the warning controller may be disposed in the body unit.

The warning controller may be independent and separated from the first output generator.

The first output performed by the first output generator may include at least one of sound, vibration, and light.

The second output performed by the second output generator may include at least one of sound, vibration, an image, and light.

The first output and the second output may be different in kind from each other.

The first output maybe first sound, and the second output may be second sound different from the first sound.

The biological information monitoring system may further include: a first driver which drives the first output generator; and a second driver which drives the second output generator. The detector may be placed on an input side of the second driver and detect the alarm signal at least one of at an input side and an output side of the first driver.

The biological information monitoring system may further include: a first driver which drives the first output generator; and a second driver which drives the second output generator. The detector may be placed on an output side of the second driver and detects the alarm signal at least one of at an input side and an output side of the first driver.

DETAILED DESCRIPTION OF EMBODIMENTS

Figure 1:
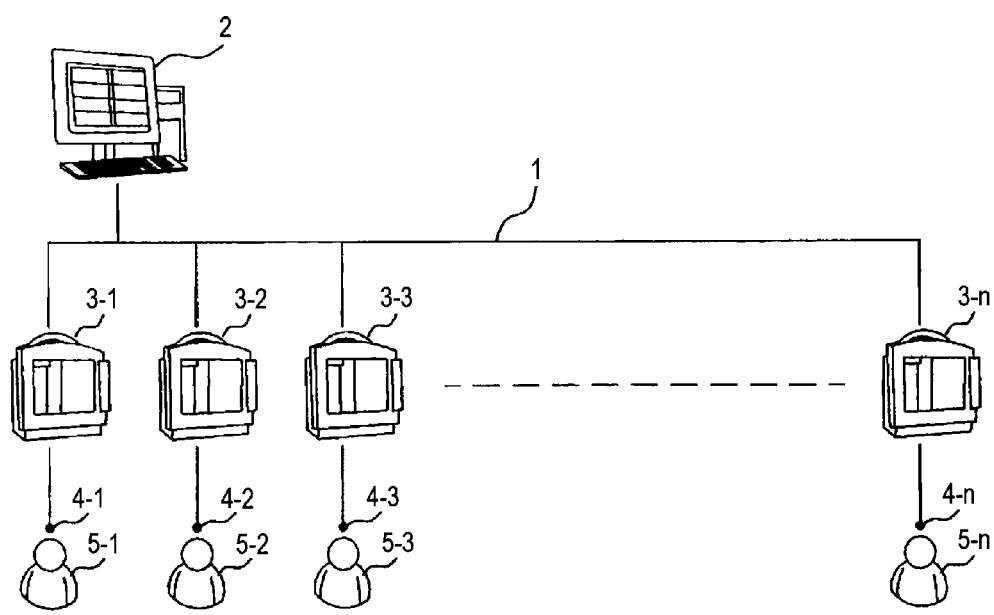
FIG. 1 is a diagram showing a first embodiment of the biological information monitoring system of the invention.

Hereinafter, embodiments of the biological information monitoring system of the invention will be described with reference to the accompanying drawings. In figures, identical components are denoted by the same reference numerals, and duplicate description will be omitted. FIG. 1 is a diagram showing a first embodiment of the biological information monitoring system of the invention. The biological information monitoring system has a configuration where a central monitor 2 and a plurality of bedside monitors 3-1, 3-2, 3-3, . . . , 3-n are connected to one another through a wired or wireless network 1.

Sensors 4-1, 4-2, 4-3, . . . , 4-n which obtain biological information of at least one or more parameters such as the heart rate, the blood pressure, and the blood oxygen saturation are connected respectively to the bedside monitors 3-1, 3-2, 3-3, . . . , 3-n so as to obtain biological information from patients 5-1, 5-2, 5-3, . . . , 5-n. Although not illustrated, alternatively, a plurality of sensors maybe connected from one bedside monitor to one patient.

The biological information which is obtained in each of the sensors 4-1, 4-2, 4-3, . . . , 4-n is compared in the corresponding one of the bedside monitors 3-1, 3-2, 3-3, . . . , 3-n with, for example, the threshold of a parameter which is previously set. When the biological information exceeds the threshold (or falls below the threshold), an alarm signal (a vital alarm) is sent together with the biological information to the network 1. An alarm signal may be generated in the case where an electrode is detached from the patient, the sensor is attached in an inadequate state, or the noise level is high (a technical alarm), or by operating an apparatus such as a nurse call apparatus which is used for notifying the observer of an abnormality when, for example, the patient feels a pain or the like. Each of the bedside monitors 3-1, 3-2, 3-3, . . . , 3-n includes an alarm generator 8 for generating an alarm signal indicative of such an abnormality.

Alternatively, the alarm generator 8 may not be disposed in the bedside monitors 3-1, 3-2, 3-3, . . . , 3-n, and may be disposed in the central monitor 2.

Figure 2:
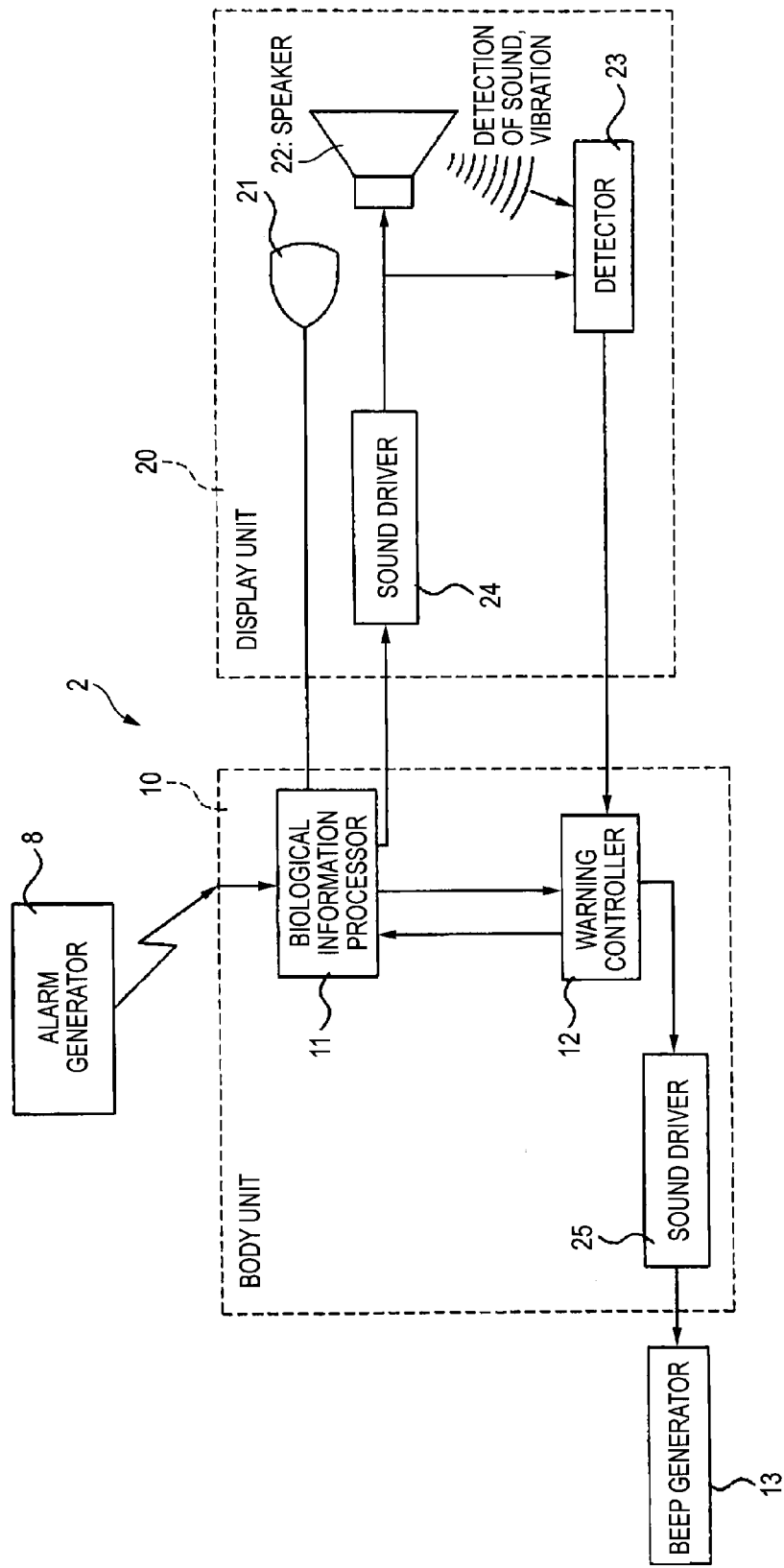
FIG. 2 is a diagram showing a part of the first embodiment of the biological information monitoring system of the invention.

FIG. 2 shows the configuration of the biological information monitoring system of the first embodiment. The central monitor 2 includes a body unit 10 and a display unit 20. The body unit 10 sends display information to the display unit 20. The body unit 10 includes a biological information processor 11 and a warning controller 12. Although not illustrated, alternatively, the body unit 10 may further include a sound driver for performing an output to a speaker 22. The display unit 20 includes an LCD display 21, the speaker 22, a detector 23, and a sound driver 24. In the body unit 10, a sound driver 25, and a beep generator (speaker) 13 are internally or externally disposed. Preferably, the beep generator 13 may perform a warning output by means of a beep sound which is different from a sound output from the speaker 22.

Figure 3:
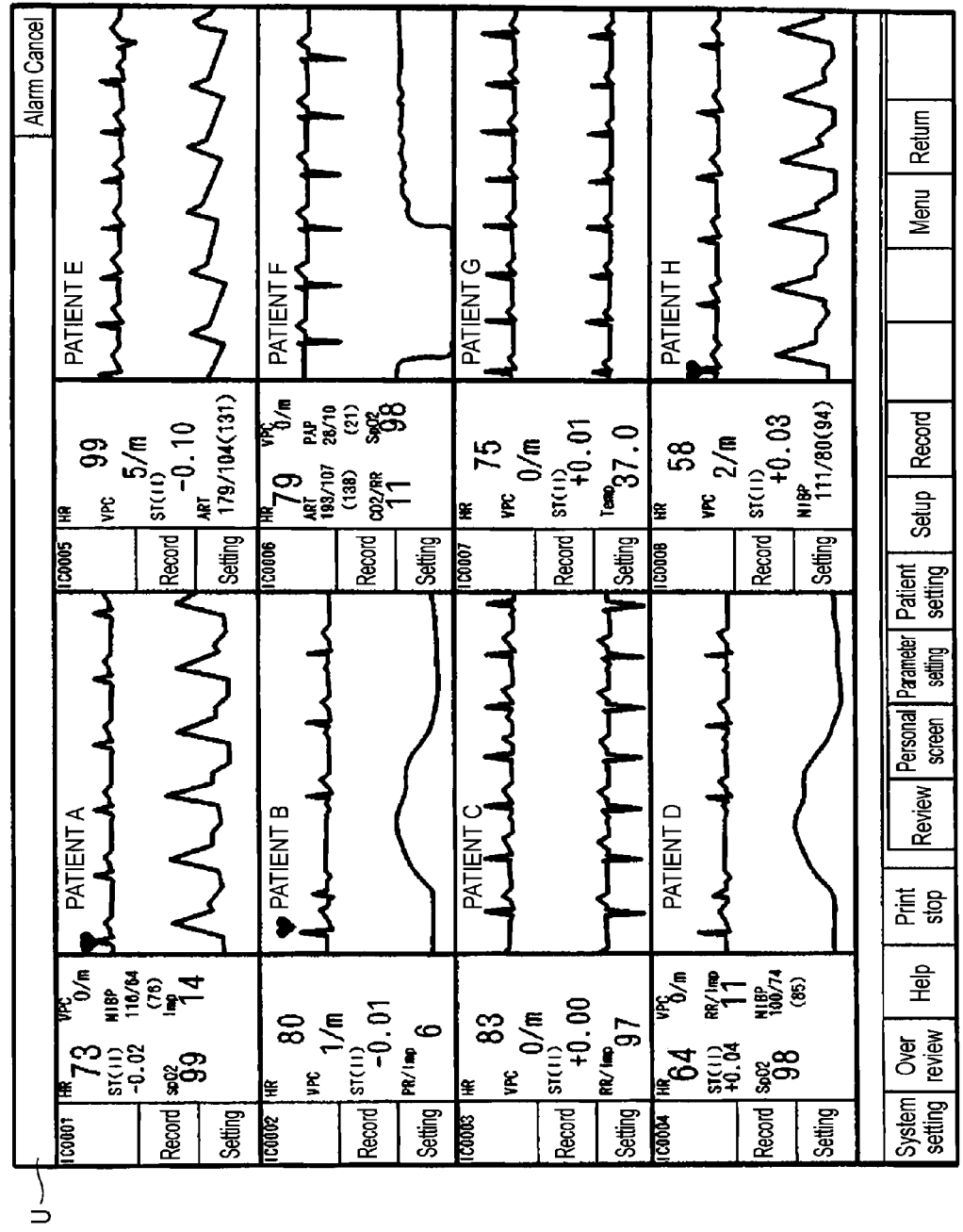
FIG. 3 is a view showing an example of a display in a part of the first embodiment of the biological information monitoring system of the invention.

The biological information processor 11 receives a biological signal via the network 1, process the signal to convert it to information for displaying an image, and sends the information to the LCD display 21 to display the biological information of the patient as shown in, for example, FIG. 3. The biological information processor 11 further receives the alarm signal from the alarm generator 8, converts the signal to an alarm signal for causing the central monitor 2 to perform an alarm output, and sends the alarm signal to the sound driver 24 via a sound driver (not shown). When the sound driver 24 receives the alarm signal from the biological information processor 11, the sound driver drives the speaker 22 to generate a warning sound.

The biological information processor 11 further sends the alarm signal or a notification signal based on the alarm signal and indicative of presence/absence of the alarm signal, to the warning controller 12, thereby notifying the warning controller 12 that an alarm is generated.

The biological information processor 11 displays images respectively corresponding to the the biological information of the patients which is sent from the bedside monitors 3-1, 3-2, 3-3, . . . , 3-n, on the LCD display 21, while splitting the images into, for example, eight-divided small frames as shown in FIG. 3. When the biological information processor 11 receives the alarm signal from the alarm generator 8, for example, the biological information processor 11 causes the image of the small frame corresponding to the patient to blink, thereby performing a warning display. When the alarm generator 8 sends the alarm signal, the speaker 22 generates the warning sound, and the warning display is performed on the LCD display 21.

The detector 23 disposed in the display unit 20 detects the state of the alarm output which is performed by the speaker 22. Alternatively, the detector 23 may detect presence/absence of the alarm signal in a path from the alarm generator 8 to the speaker 22. In the embodiment, the detector 23 includes a sensor which detects at least one of the sound and vibration of the speaker, and light, so as to detect whether the speaker 22 generates sound or vibration which is the alarm output at a level that is higher than a predetermined level or not (whether the alarm output is at a required level or not). The detection of light maybe performed in the following manner. In the case where an alarm indicator is provided instead of the speaker 22, for example, the detector 23 may detect the color or blinking intervals of light emitted from the alarm indicator.

The output of the detector 23 is sent to the warning controller 12. In the case where the warning controller 12 receives the alarm signal from the biological information processor 11, when the signal sent from the detector 23 indicates that the alarm output from the speaker 22 is not at the required level, the warning controller 12 controls the sound driver 25 so that the beep generator 13 performs the warning output. Namely, not only in the case of a failure of the path of the alarm signal or the speaker 22, but also the case where the speaker 22 is set to a low sound volume or to mute, the alarm output does not reach the required level, and the detector 23 performs the predetermined output corresponding to the state where the alarm output is not at the required level. In response to the output, the warning controller 12 controls the sound driver 25 so that the beep generator 13 performs the warning output.

In the case where the detector 23 receives the alarm signal in the path from the alarm generator 8 to the speaker 22 (in the case where the alarm signal is present), when the detected output amount of the alarm output by the speaker 22 is not at the predetermined level, the warning controller 12 may control the sound driver 25 so that the beep generator 13 performs the warning output. The warning controller 12 employs a configuration where at least one of the alarm signal generated by the alarm generator 8, and a notification signal based on the alarm signal and indicative of presence/absence of the alarm signal is used as a determination reference.

The case where, although the detector 23 receives the predetermined alarm signal generated by the alarm generator 8, or the notification signal based on the alarm signal and indicative of presence/absence of the alarm signal, the predetermined signal is not transmitted from the detector 23 to the warning controller 12 (an absence signal), or that where, although the warning controller 12 receives the predetermined signal from the detector 23, the predetermined alarm signal generated by the alarm generator 8, or the notification signal based on the alarm signal and indicative of presence/absence of the alarm signal is not transmitted to the warning controller 12 maybe considered. Therefore, it maybe considered that the former case is caused by an abnormality (failure) in the path from the biological information processor 11 to the warning controller 12 through the detector 23, and the latter case is caused by an abnormality (failure) in the path between the biological information processor 11 and the warning controller 12. Consequently, it is possible to locate the place where the abnormality (failure) is caused.

In the reception, transmission, and sending, the warning controller 12 may include the reference of a shared memory of the biological information processor 11, that of information due to a function call, or the like.

As described above, in the case where, although the warning output is performed by the beep generator 13 and the alarm signal is generated, the speaker 22 does not perform the warning output at the predetermined level, the beep generator 13 performs the warning output, so that, even in the case where an operation of reducing the sound volume or turning off the warning output is performed or a failure such as slipping off or breakage of a cable occurs, it is possible to surely notify that the warning state is caused. Furthermore, the warning controller 12 receives the signal which is to be sent in the case where the detector 23 detects that the alarm signal is present, and that the alarm output from the speaker 22 is not at the required level, and sends a warning screen request to the biological information processor 11.

Figure 4:
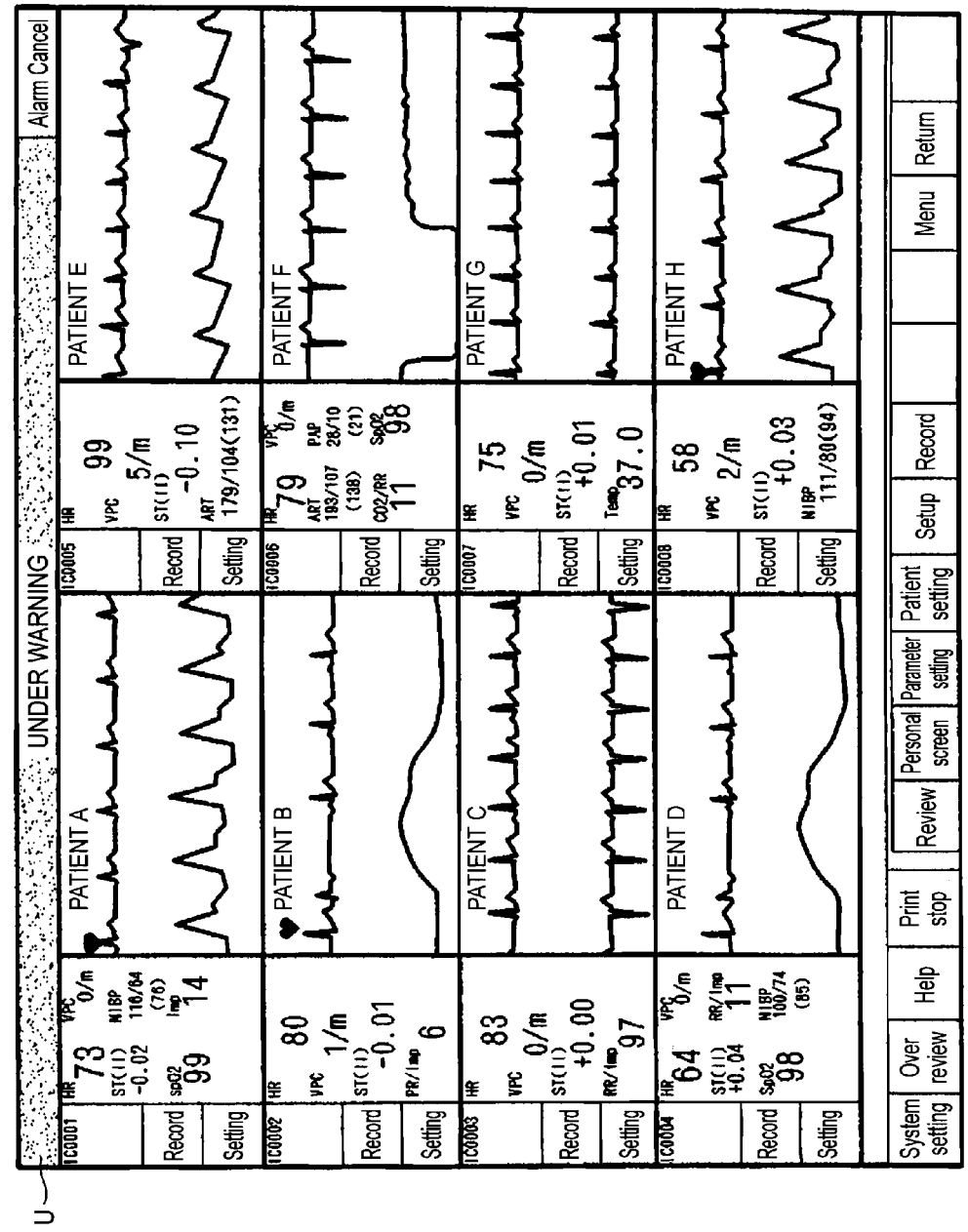
FIG. 4 is a view showing an example of a display of a warning state in a part of the first embodiment of the biological information monitoring system of the invention.

The biological information processor 11 which receives the warning screen request may modify the screen which is currently displayed on the LCD display 21 as shown in FIG. 3, so as to display a message such as "Under warning" notifying that the warning state is set, in an uppermost frame U of the image as shown in FIG. 4 or the small frame of the corresponding patient (this display state is not shown). In this case, a blinking display may be performed so as to notify that the warning state is set. In this way, warning based on sound, and that based on a display are performed to prevent a situation where, even warning is not produced by the speaker 22 which should originally perform a warning output, the observer does not notice the warning, from occurring, thereby ensuring safety of the patient.

Figure 5:
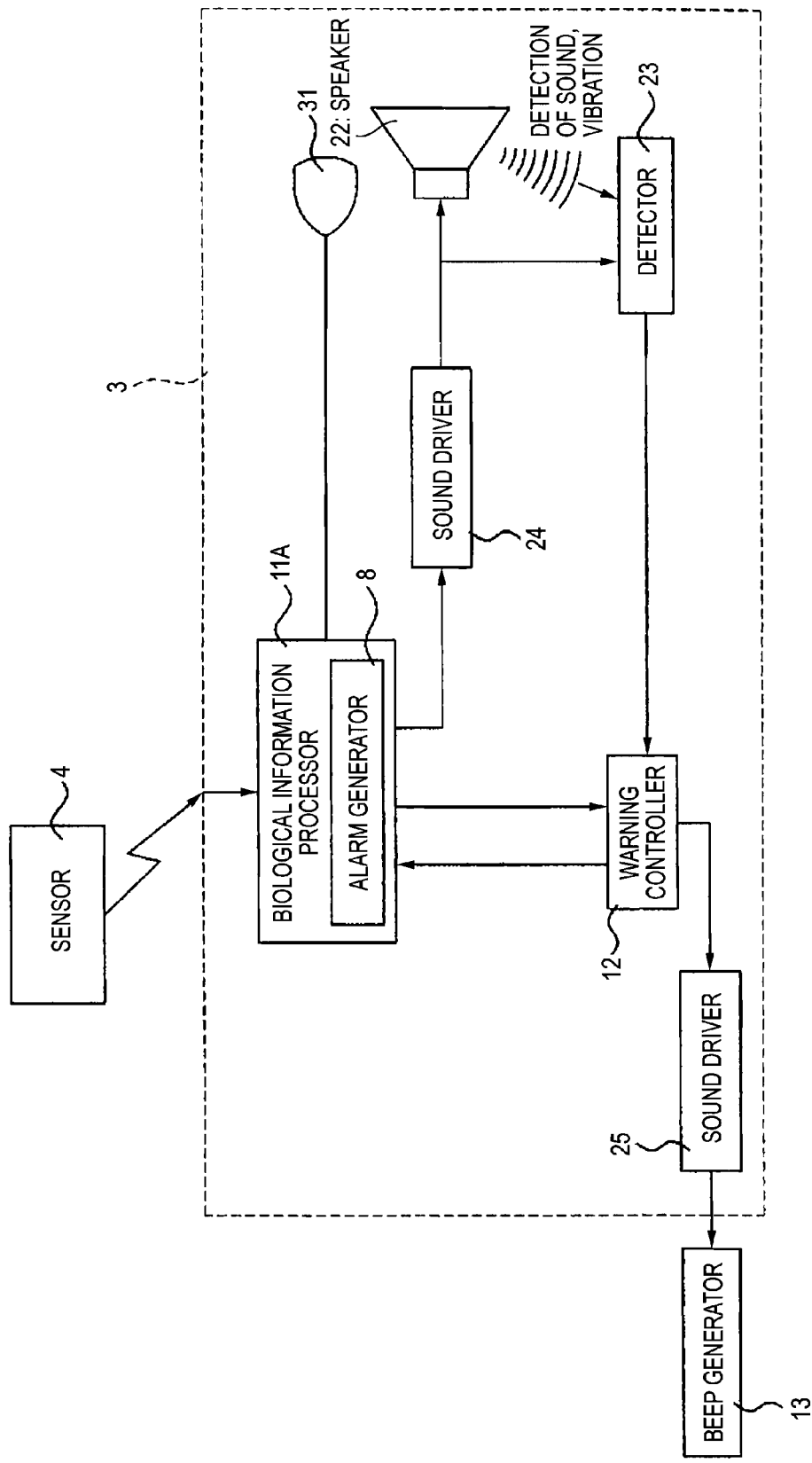
FIG. 5 is a diagram showing a part of a second embodiment of the biological information monitoring system of the invention.

FIG. 5 shows the configuration of a biological information monitoring system of a second embodiment. In the biological information monitoring system, the bedside monitor 3 includes a biological information processor 11A, the warning controller 12, an LCD display 31, the speaker 22, the detector 23, and the sound driver 24, 25. Furthermore, the beep generator (speaker) 13 is internally or externally disposed. The biological information processor 11A includes the alarm generator 8. The biological signal obtained by the sensor 4 (4-1, 4-2, 4-3, . . . , 4-n) is collected by the biological information processor 11A.

The biological signal collected by the biological information processor 11A is converted by, for example, digitization to biological information, and the biological information is compared with a threshold by the alarm generator 8. When the biological information exceeds the threshold (or falls below the threshold), an alarm signal is sent to the sound driver 24. The biological information processor 11A processes the biological information to convert it to information for displaying an image, and sends the information to the LCD display 31 to display the biological information of the patient to which the sensor 4 is attached, as shown in, for example, FIG. 6.

Also in the embodiment, the detector 23 detects the state of the alarm output which is performed by the speaker 22. It is a matter of course that the detector 23 may detect presence/absence of the alarm signal in the path from the alarm generator 8 to the speaker 22. The output of the detector 23 is sent to the warning controller 12. In the case where the warning controller 12 receives the alarm signal from the biological information processor 11A, when the signal sent from the detector 23 indicates that the alarm output from the speaker 22 is not at the required level, the warning controller controls the sound driver 25 so that the beep generator 13 performs the warning output.

Figure 6:
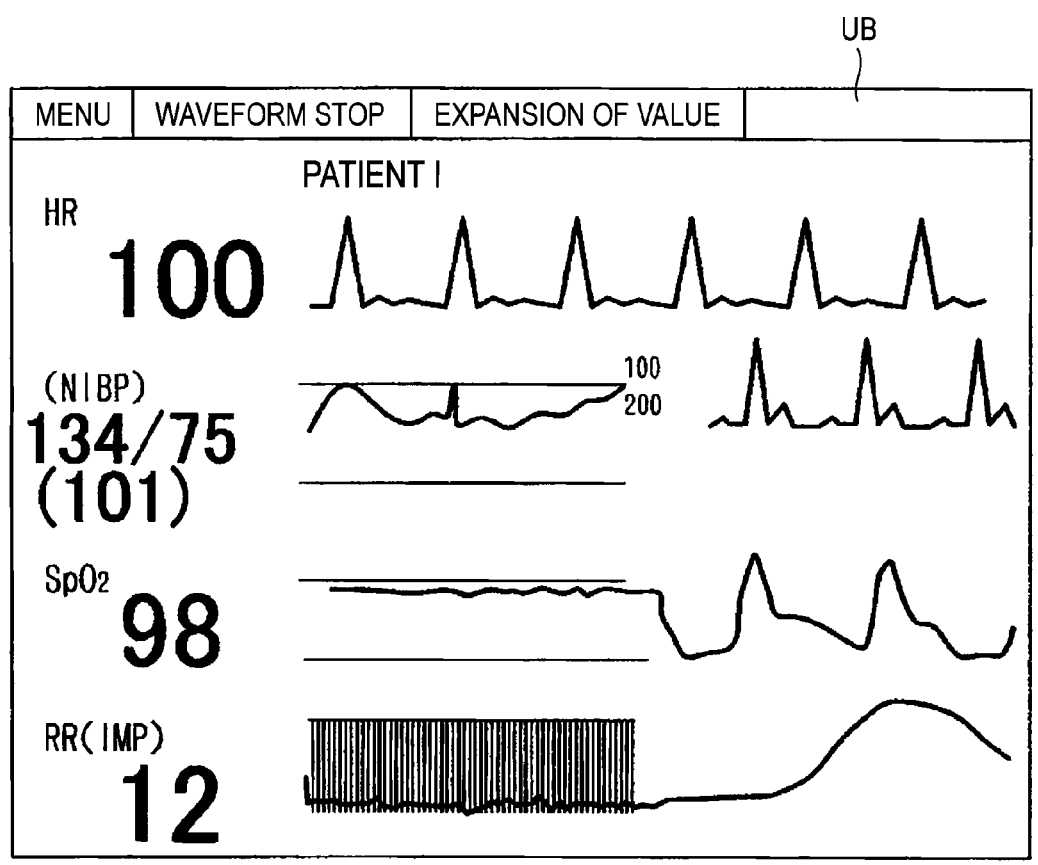
FIG. 6 is a view showing an example of a display in a part of the second embodiment of the biological information monitoring system of the invention.

In the case where the warning controller 12 receives the alarm signal from the biological information processor 11A, when the warning controller 12 receives from the detector 23 the signal which is to be sent when it is detected that the alarm output from the speaker 22 is not at the required level, the warning controller 12 sends the warning screen request to the biological information processor 11A. The biological information processor 11A which receives the warning screen request modifies the screen which is currently displayed on the LCD display 31 as shown in FIG. 6, so as to display a message such as "Under warning" notifying that the warning state is set, in an uppermost frame UB of the image in the same manner as described with reference to FIG. 4, and causes the uppermost frame UB to be blinking-displayed, thereby notifying that the warning state is set. In this way, notification of warning based on sound, and that based on a display are performed to prevent a situation where, even when warning is not produced by the speaker 22 which should originally perform a warning output, the observer does not notice the warning, from occurring, thereby ensuring safety of the patient.

Figure 7:
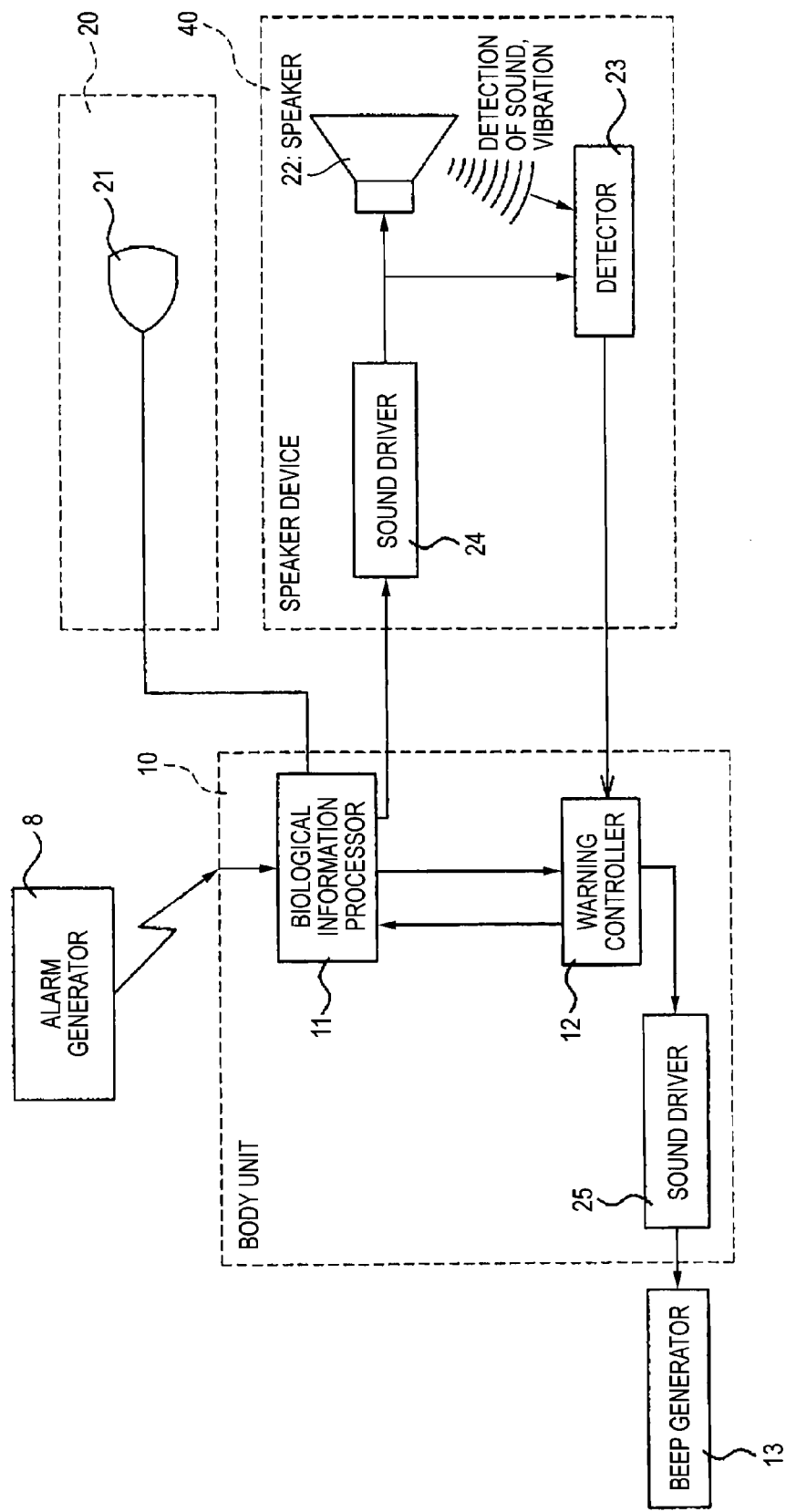
FIG. 7 is a diagram showing a part of a third embodiment of the biological information monitoring system of the invention.

FIG. 7 shows the configuration of a biological information monitoring system of a third embodiment in which the configuration of the biological information monitoring system of the first embodiment is changed. In the embodiment, an external speaker device 40 is disposed in the configuration of the biological information monitoring system shown in FIG. 2, and the speaker 22, and the detector 23, and the sound driver are disposed in the speaker device 40. The other configuration is identical with that of the biological information monitoring system of the first embodiment.

Also in the biological information monitoring system of third embodiment, in the case where the warning controller 12 receives the alarm signal from the biological information processor 11, when the signal sent from the detector 23 indicates that the alarm output from the speaker 22 is not at the required level, the warning controller controls the sound driver 25 so that the beep generator 13 performs the warning output. A message such as "Under warning" notifying that the warning state is set may be displayed in the uppermost frame U of the image as shown in FIG. 4 or the small frame of the corresponding patient (this display state is not shown). In this case, a blinking display may be performed so as to notify that the warning state is set. The configuration of the third embodiment is not restricted to a central monitor, and may be applied to a bedside monitor or the like.

Figure 8:
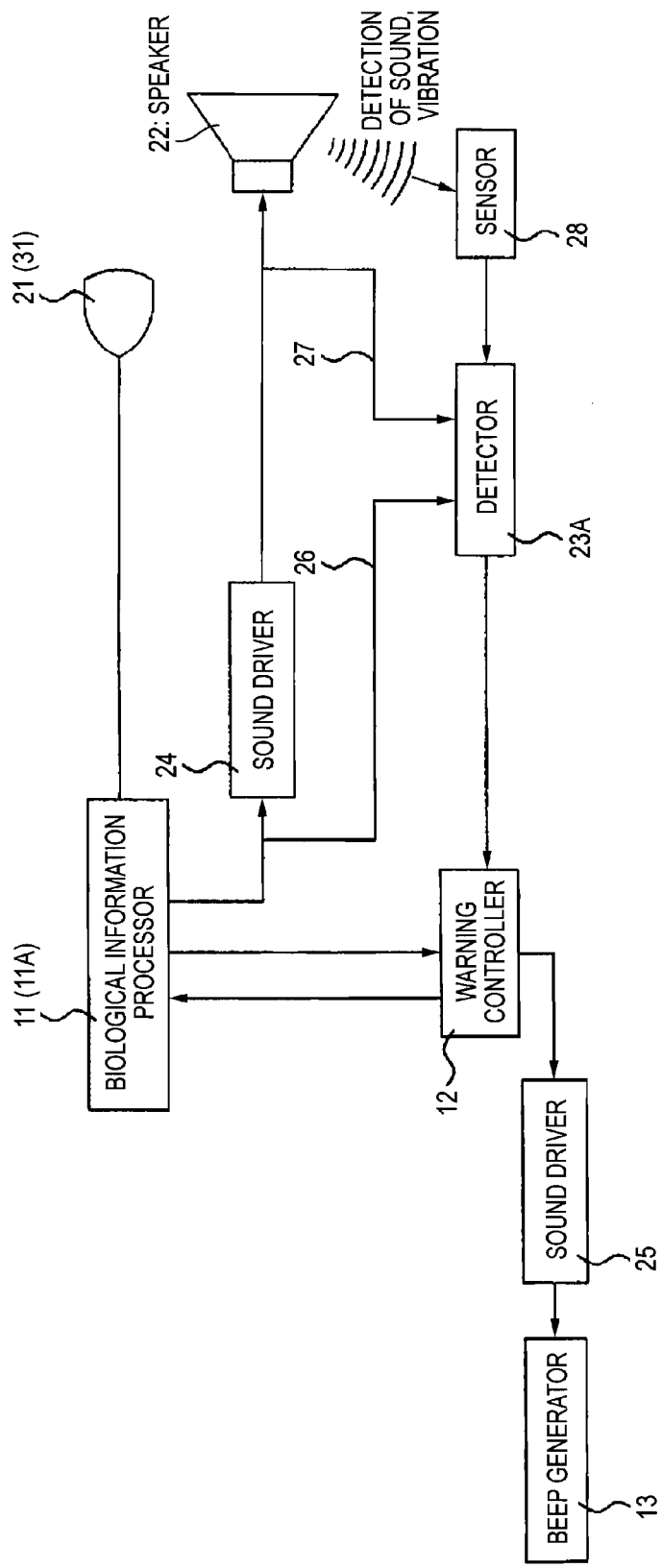
FIG. 8 is a diagram showing a part of a fourth embodiment of the biological information monitoring system of the invention.

FIG. 8 shows the configuration of a biological information monitoring system of a fourth embodiment in which the configurations of the biological information monitoring systems of the first to third embodiments are changed. The embodiment employs a configuration where a sensor 28 which detects vibration and sound is disposed to perform detection, and an output signal of the sensor 28 is sent to a detector 23A. The detector 23A is configured so as to obtain an alarm signal 26, 27 from the input and output sides of the sound driver 24. Also in the configuration, similarly with the biological information monitoring systems of the first to third embodiments, warning based on sound, and that based on a display are performed to prevent a situation where, even when a warning is not produced by the speaker 22 which should originally perform a warning output, the observer does not notice the warning, from occurring, thereby ensuring safety of the patient. Particularly, also in the case where a fault occurs in subsequent to the sound driver 24, warning is performed, and there is an advantage that a signal indicative of a warning state can be surely output.

Figure 9:
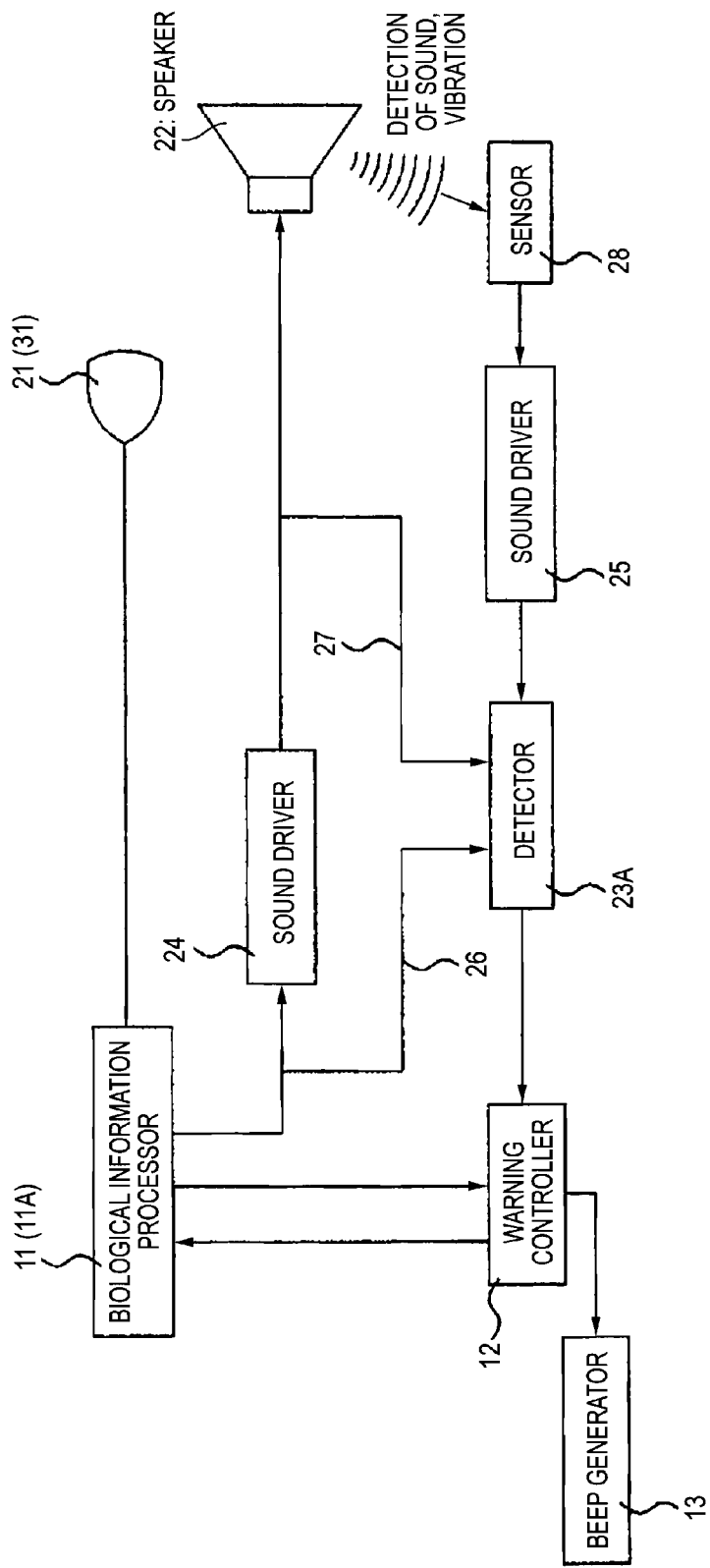
FIG. 9 is a diagram showing a part of a fifth embodiment of the biological information monitoring system of the invention.

FIG. 9 shows the configuration of a biological information monitoring system of a fifth embodiment in which the configuration of the biological information monitoring system of the fourth embodiment is changed. In the biological information monitoring system of the fourth embodiment, the detector 23A is disposed on the input side of the sound driver 25. In the embodiment, by contrast, the detector 23A is disposed on the output side of the sound driver 25. The other configuration is identical with that of the biological information monitoring system of the fourth embodiment. Also according to the configuration, it is possible to attain functions and effects which are similar to those of the biological information monitoring system of the fourth embodiment. Also the configuration of the fourth embodiment is not restricted to a central monitor, and may be applied to a bedside monitor or the like.

In the above, the embodiments using the speaker 22, the beep generator 13 and the LCD display 21 are described. Alternatively, any device which outputs at least one of sound, vibration, and light maybe used instead of the speaker 22, and that which outputs at least one of sound, vibration, an image, and light may be used instead of the beep generator 13 and the LCD display 21.

Figure 10:
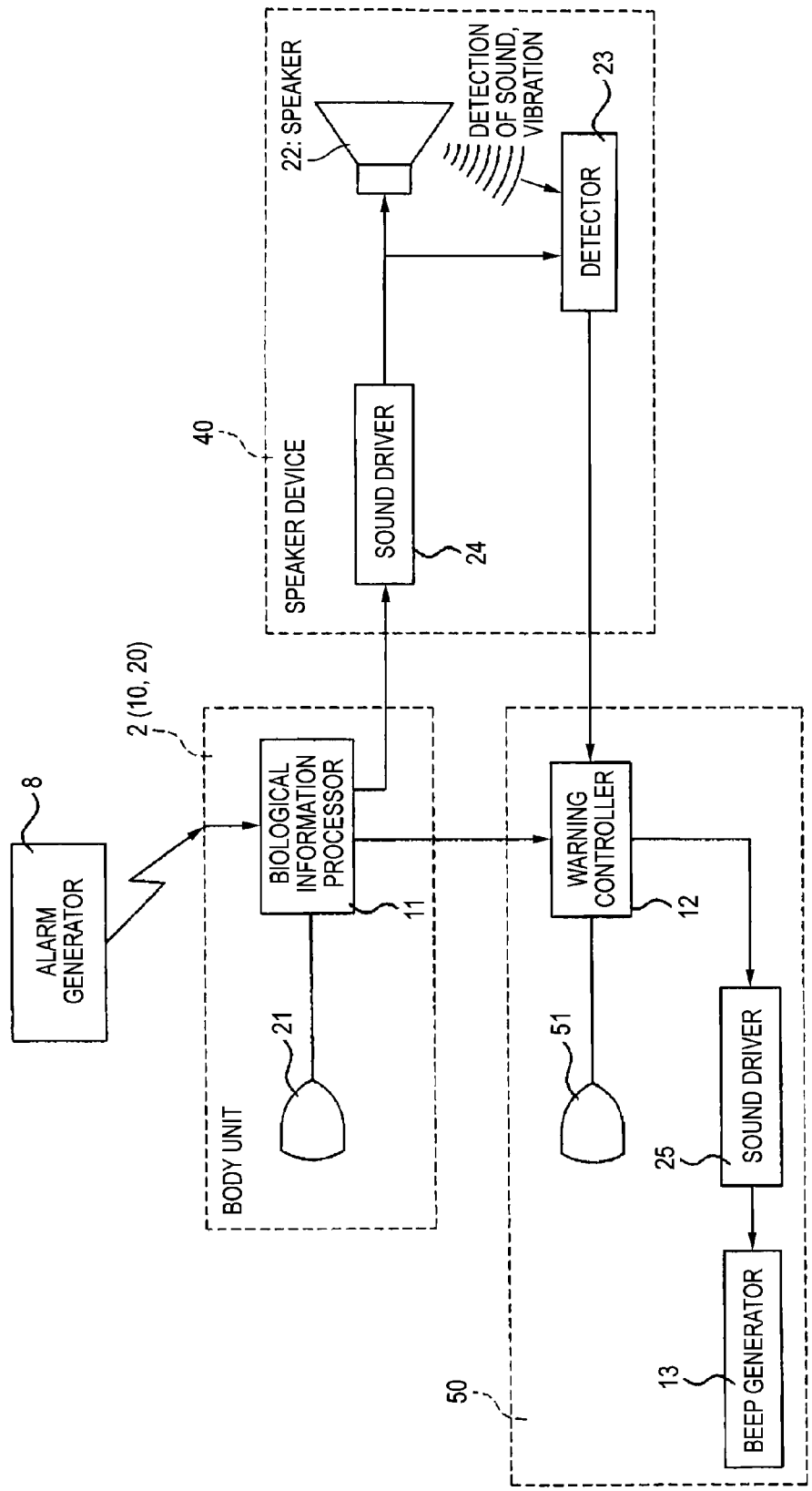
FIG. 10 is a diagram showing a part of a sixth embodiment of the biological information monitoring system of the invention.

FIG. 10 shows the configuration of a biological information monitoring system of a sixth embodiment. The biological information monitoring system of the sixth embodiment includes the central monitor 2, the speaker device 40, and a warning device 50. The central monitor 2 includes the body unit 10 and the display unit 20, and further includes the biological information processor 11 and the LCD display 21.

The speaker device 40 includes the sound driver 24, the speaker 22, and the detector 23. The warning device 50 includes the warning controller 12, the sound driver 25, the beep generator 13, and a display device 51 having a display screen such as an LCD, and a display controller. The central monitor 2 and the warning device 50 are connected to each other through a wired or wireless network, and the speaker device 40 and the warning device 50 are connected to each other through a wired or wireless network. Therefore, the warning device 50 may be placed in a remote place.

The biological information processor 11 receives a biological signal through the network 1, processes the signal to convert it to information for displaying an image, and sends the information to the LCD display 21 to display biological information of the patients as shown in, for example, FIG. 3. The biological information processor 11 further receives the alarm signal from the alarm generator 8, converts the signal to an alarm signal for causing the speaker device 40 to perform an alarm output, and sends the alarm signal to the sound driver 24. The biological information processor 11 further sends the alarm signal also to the warning controller 12.

The detector 23 detects the state of the alarm output which is performed by the speaker 22. Alternatively, the detector 23 may detect presence/absence of the alarm signal in a path from the alarm generator 8 to the speaker 22. The output of the detector 23 is sent to the warning controller 12.

In the case where the warning controller 12 receives the alarm signal from the biological information processor 11, when the signal sent from the detector 23 indicates that the alarm output from the speaker 22 is not at the required level, the warning controller 12 controls the sound driver 25 so that the beep generator 13 performs the warning output.

As described above, in the case where, although the warning output is performed by the beep generator 13 and the alarm signal is generated, the speaker 22 does not perform the warning output, the beep generator 13 performs the warning output, so that, even in the case where an operation of reducing the sound volume or turning off the warning output is performed or a failure such as slipping off or breakage of a cable occurs, it is possible to surely notify that the warning state is caused. Furthermore, the display device 51 actually performs a display notifying that an alarm output is performed, by means of characters, blinking light, or the like, so that notification of a warning state can be executed through the eyes.

In all the embodiments, the biological information processor 11 sends the alarm signal to the warning controller 12. Alternatively, a configuration where the biological information processor 11 does not send the alarm signal to the warning controller 12 may be employed. Also in the configuration, the state of the alarm output detected by the detector 23 can be used as a determination reference, and the beep generator 13 can be controlled so as to perform the warning output. Also in the configuration, in the case where, although the alarm signal is generated, the speaker 22 does not perform the warning output, the beep generator 13 performs the warning output, so that, even in the case where an operation of reducing the sound volume or turning off the warning output is performed or a failure such as slipping off or breakage of a cable occurs, it is possible to surely notify that the warning state is caused. Furthermore, the display device 51 actually performs a display notifying that an alarm output is performed, by means of characters, blinking light, or the like, so that notification of a warning state can be executed through the eyes. Alternatively, the system may be configured so that the warning output is performed on the basis of at least one kind of alarm signal among an alarm signal indicative of an abnormality (vital alarm) of biological information, that indicative of an abnormality (technical alarm) of an apparatus or a sensor, or that indicative of an abnormality which is noticed by the patient, and which is informed by operating an apparatus such as a nurse call apparatus.

According to an aspect of the invention, in accordance with the state of the alarm output, the system can perform the warning output which is independent from the alarm output.

According to an aspect of the invention, in a case such as that where the warning output is not performed although the alarm signal is produced, the system can back up the case to perform the warning output.

According to an aspect of the invention, in the case where the alarm is caused by a failure of an apparatus such as slipping off or breakage of a cable, an output indicative of a warning state can be surely performed. Moreover, it is possible to know a part of the path of the alarm signal where the failure occurs, by the presence/absence of the alarm signal detected by the detector.

According to an aspect of the invention, the warning controller uses the alarm signal detected by the detector and the detected alarm output, as the determination reference. Also in the case where the alarm is caused by an artificial operation such as that of reducing the sound volume or turning off the warning output, therefore, a signal indicative of an alarm state can be surely output.

According to an aspect of the invention, a first output signal which is output as the alarm output and a second output signal which is output as the warning output are different in kind from each other. Even in the case where, for example, the first output signal which is an audible signal is not adequately output in a noisy environment, therefore, a signal indicative of a warning state can be surely output to the observer by means of the second output signal which is an optical signal due to light or a display.

It is said that, when a warning is output excessively frequently, the sensitivity of the observer to a warning is lowered, and the observer fails to notice the warning. According to an aspect of the invention, the second output signal is a sound signal which is different from the first output signal that is output as a usual warning. Therefore, a signal which easily attracts the attention of the observer, and which is indicative of a warning state can be surely output.

According to an aspect of the invention, the warning controller and the speaker are respectively configured by devices which are independent and different from each other, and can be disposed outside an existing apparatus. Therefore, the system can be applied also to an apparatus which is already disposed, and hence is high in versatility. Even in an existing apparatus, a signal indicative of a warning state can be surely output to the observer at a minimum cost.

According to an aspect of the invention, in response to a fault or abnormality of in a transmission path of the alarm signal, therefore, a signal indicative of a warning state can be surely output.

What is claimed is:

1. A biological information monitoring system comprising:
an alarm generator which generates an alarm signal indicative of an abnormality of biological information of a patient, or an abnormality of a unit related to monitoring of biological information of a patient, or an abnormality due to an operation of a unit related to monitoring of biological information of a patient;
a biological information processor that receives the alarm signal from the alarm generator, converts the alarm signal to an alarm output, outputs the alarm output along a first data path, and outputs one of the alarm output and a notification signal indicating presence of the alarm output along a second data path;
a first output generator connected to the biological information processor along the first data path, the first data path beginning at the biological information processor and terminating at the first output generator;
a sound driver which receives the alarm output from the biological information processor along the first data path and drives the first output generator to output a first alarm based on the alarm output, the sound driver connected between the biological information processor and the first output generator along the first data path;
a detector which detects the alarm output at an input side of the sound driver and an output side of the sound driver along the first data path and outputs an output signal indicating presence of the alarm output detected along the first data path;
a second output generator which outputs a second alarm independent from the first alarm; and
a warning controller directly connected to the biological information processor along the second data path, the second data path beginning at the biological information processor and terminating at the warning controller which receives (i) a first input of the one of the alarm output and the notification signal indicating presence of the alarm output from the biological information processor along the second data path and (ii) a second input of the output signal from the detector, determines a malfunction condition that exists when (a) the first input is received and the second input is not received or (b) the first input is not received and the second input is received, and controls the second output generator to output the second alarm in response to determining the malfunction condition.

2. The biological information monitoring system according to claim 1, wherein the alarm generator is disposed in one of a remote device which is remotely connected to a monitor device which monitors the biological information of the patient and the monitor, and the first output generator and the detector are disposed in the remote device.

3. The biological information monitoring system according to claim 1, wherein the alarm generator, the first output generator, the detector, the second output generator, and the warning controller are disposed in a monitor device which monitors the biological information of the patient.

4. The biological information monitoring system according to claim 1, further comprising:
a display unit; and
a body unit which sends display information to the display unit,
wherein the first output generator and the detector are disposed in the display unit, and the second output generator and the warning controller are disposed in the body unit.

5. The biological information monitoring system according to claim 1, wherein the warning controller is independent and separated from the first output generator.

6. The biological information monitoring system according to claim 1, wherein the first alarm output by the first output generator includes at least one of sound, vibration, and light.

7. The biological information monitoring system according to claim 1, wherein the second alarm output by the second output generator includes at least one of sound, vibration, an image, and light.

8. The biological information monitoring system according to claim 1, wherein the first alarm and the second alarm are different in kind from each other.

9. The biological information monitoring system according to claim 1, wherein the first alarm is a first sound, and the second alarm is a second sound different from the first sound.

10. The biological information monitoring system according to claim 1, further comprising:
a first driver which drives the first output generator; and
a second driver which drives the second output generator,
wherein the detector is placed on an input side of the second driver and detects the alarm signal at least one of at an input side and an output side of the first driver.

11. The biological information monitoring system according to claim 1, further comprising:
a second driver which drives the second output generator, wherein the detector is connected to an output side of the second driver.

\* \* \* \* \*